(12) United States Patent
Martel et al.

(10) Patent No.: US 9,364,455 B2
(45) Date of Patent: Jun. 14, 2016

(54) COMBINATION OF A PROSTAGLANDIN RECEPTOR AGONIST AND AN MC1R RECEPTOR AGONIST FOR THE TREATMENT AND/OR PREVENTION OF PIGMENTATION DISORDERS

(71) Applicant: GALDERMA RESEARCH & DEVELOPMENT, Biot (FR)

(72) Inventors: Philippe Martel, Biot (FR); Itaru Suzuki, Shizuoka (JP); Johannes Voegel, Châteauneuf de Grasse (FR); Philippe Andres, Peymeinade (FR); Sandrine Rethore, Valbonne (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 14/365,851

(22) PCT Filed: Dec. 17, 2012

(86) PCT No.: PCT/EP2012/075829
§ 371 (c)(1),
(2) Date: Jun. 16, 2014

(87) PCT Pub. No.: WO2013/087936
PCT Pub. Date: Jun. 20, 2013

(65) Prior Publication Data
US 2014/0371147 A1    Dec. 18, 2014

(30) Foreign Application Priority Data

Dec. 16, 2011 (FR) ...................................... 11 61779

(51) Int. Cl.
| | | |
|---|---|---|
| A61K 38/34 | (2006.01) | |
| C07K 14/68 | (2006.01) | |
| A61K 31/216 | (2006.01) | |
| A61K 45/06 | (2006.01) | |
| A61K 31/165 | (2006.01) | |
| A61K 31/192 | (2006.01) | |
| A61K 31/4178 | (2006.01) | |
| A61K 31/454 | (2006.01) | |
| A61K 38/33 | (2006.01) | |
| A61K 38/35 | (2006.01) | |

(52) U.S. Cl.
CPC ............ *A61K 31/216* (2013.01); *A61K 31/165* (2013.01); *A61K 31/192* (2013.01); *A61K 31/4178* (2013.01); *A61K 31/454* (2013.01); *A61K 38/33* (2013.01); *A61K 38/34* (2013.01); *A61K 38/35* (2013.01); *A61K 45/06* (2013.01)

(58) Field of Classification Search
CPC ............ A61K 2300/00; A61K 31/165; A61K 31/192; A61K 31/216; A61K 31/4178; A61K 31/454; A61K 38/33; A61K 38/34; A61K 38/35; A61K 45/06
See application file for complete search history.

(56) References Cited

U.S. PATENT DOCUMENTS

| 4,254,145 | A | * | 3/1981 | Birnbaum ............ A61K 9/0014 |
| | | | | 514/530 |
| 5,905,091 | A | | 5/1999 | Fuller |
| 2011/0130705 | A1 | * | 6/2011 | Wolgen ................ A61K 9/0019 |
| | | | | 604/20 |

FOREIGN PATENT DOCUMENTS

| FR | 2937973 A1 | 5/2010 | |
| LT | 4369 B | 8/1988 | |
| WO | 2008/108549 A1 | 9/2008 | |
| WO | WO2010/052253 | * 5/2010 | ........... C07D 410/12 |

OTHER PUBLICATIONS

Anbar et al. Skin pigmentation after NB-UVB and three analogues of prostaglandin F2alpha in guinea pigs: a comparative study. JEADV. Published online: Jul. 13, 2009. abstract only, 3 pages.*
Sarangal et al. Comments regarding Abar et al. JEADV 2010: 24: 28-31. Indian Journal of Dermatology, Venereology, and Leprology, vol. 76, No. 2, Mar.-Apr. 2010, pp. 221-224, accessed online at http://www.bioline.org.br/request?dv10072 on Sep. 4, 2015, 3 pages.*
Noh et al. Three Cases of Vitiligo Showing Response to Application of Latanoprost. Korean J. Dermatol. 2010, vol. 48, No. 4, pp. 350-353. abstract only, 2 pages.*
Englsh Translation of International Search Report dated Apr. 9, 2013 corresponding to International Patent Application No. PCT/EP2012/075829, 3 pages.

* cited by examiner

*Primary Examiner* — Marcela M Cordero Garcia
(74) *Attorney, Agent, or Firm* — Dentons US LLP

(57) ABSTRACT

A combination of compounds is described for the treatment and/or prevention of skin conditions linked to hypopigmentation. Also described, is a combination product that includes at least one prostaglandin receptor agonist and at least one MC1R receptor agonist, as a medicament for use simultaneously, separately or spread out over time for the treatment and/or prevention of skin conditions linked to hypopigmentation, such as vitiligo.

18 Claims, 2 Drawing Sheets

Figure 1:
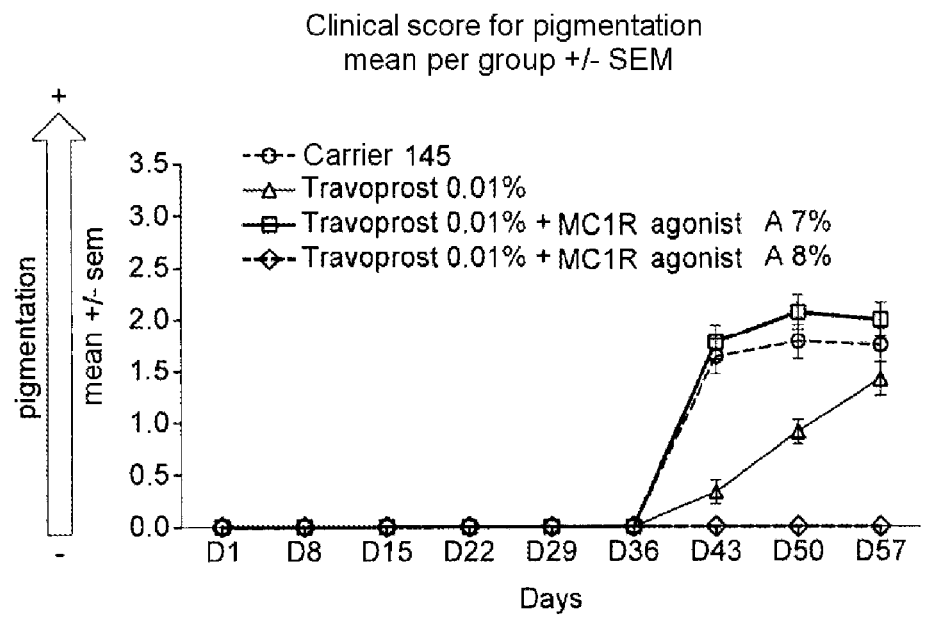

Clinical score for pigmentation
mean per group +/- SEM

AUC (D1-D57) of the clinical score for pigmentation
Mean +/- sem
(Student's t-test versus carrier 145 / Student's t test travoprost)
induction versus travopost

COMBINATION OF A PROSTAGLANDIN RECEPTOR AGONIST AND AN MC1R RECEPTOR AGONIST FOR THE TREATMENT AND/OR PREVENTION OF PIGMENTATION DISORDERS

CROSS-REFERENCE TO PRIOR APPLICATIONS

This application is a National Stage of PCT/EP2012/075829, filed Dec. 17, 2012, and designating the United States (published in English on Jun. 20, 2013, as WO 2013/087936 Al), which claims priority under 35 U.S.C. §119 to French Patent Application No. 1161779, filed Dec. 16, 2011, each hereby expressly incorporated by reference in its entirety and each assigned to the assignee hereof.

The invention relates to a combination of compounds for the treatment and/or prevention of dermatological conditions linked to hypopigmentation.

The pigmentation of human skin is the result of melanin synthesis by melanocytes. Melanocytes contain organelles called melanosomes, which are the seat of melanin biosynthesis and, more particularly, of two chemically distinct types of melanins, eumelanin, a brown-black colored pigment, and pheomelanin, a yellow-red colored pigment. Melanin synthesis, or melanogenesis, involves, schematically, the following main steps:

Tyrosine->Dopa->DOPAquinone->Dopachrome->Melanin.

Inside the melanosomes, tyrosinase is the key enzyme of melanogenesis. It is synthesized in the form of an inactive precursor, which is activated when the melanocytes are stimulated by $\alpha$-MSH via cAMP. Tyrosinase catalyzes in particular the first two steps, with the hydroxylation of tyrosine to give 3,4-dihydroxyphenylalanine (DOPA) and the oxidation of DOPA (non-free intermediate of the catalytic reaction) to give DOPAquinone.

All individuals, without phototype distinction, have approximately the same number of melanocytes for a given unaffected area of skin. The differences in terms of pigmentation are not due to the number of melanocytes, but to the properties of their melanosomes. In humans, as in other mammals, the color of the skin and body hair is mainly determined by the number, the size, the type and the mode of distribution of the melanosomes. Melanin is uniformly deposited on the internal fibrillar network of the melanosome and the opacity of the organelle increases to saturation. During the course of melanin synthesis in the melanosomes, the latter move from the perinuclear region to the end of the melanocyte dendrites. It is the melanosomes which, after migration along the dendrites, are transferred from the melanocytes to the keratinocytes and redistributed in the keratinocytes. The keratinocytes are then transported to the surface of the skin during the epidermal differentiation process and the melanin is thus distributed in the epidermis, providing browning and protection thereof (Gilchrest B A, Park H Y, Eller M S, Yaar M, Mechanisms of ultraviolet light-induced pigmentation. Photochem Photobiol 1996; 63: 1-10; Hearing V J, Tsukamoto K, Enzymatic control of pigmentation in mammals. FASEB J 1991; 5: 2902-2909).

Although the melanin content varies from one population to another, the amount of tyrosinase does not significantly vary and the tyrosinase messenger RNA content is identical in white or black skin.

Variations in melanogenesis are therefore in particular due to variations in melanocyte activity and mainly tyrosinase activity, to the type of melanin synthesized, and to the ability of the keratinocytes to phagocytose the melanosomes and to become distributed in the skin.

Furthermore, it is known that the natural pigmentation can be modulated by a large number of intrinsic or extrinsic factors. The amount and the nature of the melanins contained in human skin, and also the distribution thereof, are influenced by various factors, such as heredity, or even by exposure to physical agents such as X-rays or UV rays, to a burn, to cold and to other mechanical aggressions, or else to depigmenting chemical agents such as dermocorticoids, azelaic acid, benzoyl peroxide or hydroquinone.

Among the various possible causes of skin hypopigmentation, diffuse or circumscribed hereditary hypopigmentations or circumscribed acquired hypopigmentations which are not genetically determined can be distinguished.

More particularly, vitiligo is a chronic skin condition characterized by the appearance of matt white marks with a precise outline on the feet, the hands, the face, the lips or other parts of the body. The depigmentation may be more or less significant, and the depigmented areas may be of variable sizes. In extreme cases, the body hair or the head hair which grows inside the depigmented regions is also white. Vitiligo effects from 1% to 2% of the population. It generally appears before 20 years old (half of affected individuals developed it before this age). It is neither contagious nor does it cause the individual to feel unwell, but it may cause a certain psychological distress owing to its unattractive appearance. There are two types of vitiligo:

segmental vitiligo located unilaterally on an area of the face, of the upper part of the body, of the legs or of the arms, which generally does not progress;

generalized vitiligo, which presents with marks that are often bilateral and more or less symmetrical on areas of repeated friction or pressure and which may become more significant over the years.

People who suffer from vitiligo have a higher probability of developing other autoimmune diseases.

The depigmentation observed in vitiligo results from the disappearance of the melanocytes in the lesional areas. Several causes are responsible for this disorder: autoimmune, autocytotoxic, neural dysfunction, violent stress (Passeron and Ortonne, 2005).

Many solutions have been proposed in the field of natural coloration, by stimulation of the natural pigmentation pathways, for example using active agents which stimulate melanogenesis with or without a UV action, for instance $\alpha$-MSH or derivatives thereof or prostaglandins. Intrinsic factors, which regulate pigmentation, may also come not only from keratinocytes and fibroblasts, but also from endothelial cells and from the hormones conveyed by the blood supply, inflammatory cells and the nervous system. In keratinocytes, Foxn1 and p53 are transcription factors which regulate skin pigmentation via FGFbeta and POMC derivatives, such as $\alpha$-MSH and ACTH, respectively. Other keratinocyte activators of melanogenesis are SCF/steel factor, HGF, GM-CSF, NGF, endorphin, endothelin-1 (ET-1), prostaglandin (PG)E2/PGF2$\alpha$ and LIF. Endothelial cells are sources of endothelin-1, of prostaglandins PGE2/PGF2, and of nitric oxide, which activate skin pigmentation. Prostaglandins, thromboxanes and leukotrienes increase tyrosinase activity and are responsible for post-inflammatory hyperpigmentation. On the other hand, IL6 and TNFalpha are inhibitors of skin pigmentation. Histamine, NO, GM-CSF and $\alpha$-MSH are other factors produced during inflammation which increase melanogenesis (M. Demarchez, Melanocyte and Pigmentation, Biology of Skin, 2011).

Thus, patent document U.S. Pat. No. 5,905,091 is known, for example, which discloses the use of prostaglandins for stimulating melanin synthesis in human melanocytes in order to promote skin tanning and to increase photoprotection against UV radiation.

Patent documents WO 2010/052255 and WO 2010/052253 are also known, which disclose MC1R-modulating compounds used to treat pigmentary, both hypopigmentary and hyperpigmentary, inflammatory and immune disorders.

However, as is the case, for example, with vitiligo, the hypopigmentation or even depigmentation results from the disappearance of melanocytes in the lesional areas. Such treatments with prostaglandins or MC1R-modulating compounds may thus prove to be barely effective or even ineffective.

Moreover, UV irradiation is also well known for increasing most factors which stimulate melanogenesis. UV radiation induces an immediate response and a later response. The immediate action, after a few minutes, persists for several days, but this rapid increase in pigmentation results only from the oxidation of pre-existing pigments and from the redistribution of the melanosomes without any increase in melanogenesis. The late response to UV radiation corresponds to an increase in melanogenesis, which results from an increase in the expression of MITF, a major regulator of transcription in pigmentation, and of its downstream targets including Pmel17, MART-1, 1a tyrosinase, Tyrp1 and Tyrp2/Dct. Furthermore, epidermal melanocytes and also keratinocytes respond to UV exposure by increasing their productions of $\alpha$-MSH and ACTH, which, in turn, induce an increase in MC1R expression at the surface of melanocytes and thus stimulate melanogenesis (M. Demarchez, Melanocyte and Pigmentation, Biology of Skin, 2011).

However, any excessive UV exposure may cause structural lesions of the skin in humans. In the short-term, these lesions cause burns, weakening of the skin tissue and scars and, in the long-term, photoinduced skin aging. This photoaging, caused by degradation of the collagen present in the skin under the influence of UV radiation, manifests itself through the appearance of wrinkles and the loss of skin elasticity.

Furthermore, exposure to UV radiation, whether it is natural or artificial under UV lamps for example, is a known risk factor for skin cancer.

Considering the aforementioned, a problem addressed by the invention is that of carrying out an improved treatment of dermatological conditions linked to hypopigmentation by increasing melanogenesis.

In the context of the invention, the increase in melanogenesis is characterized by an immediate response and a later response through stimulation of the natural pigmentation pathways and an increase in the activity of these pathways. Furthermore, the subject of the invention limits any risk of structural lesions of the skin and of skin cancer in humans.

Without wishing to be bound by a particular mechanism of action, the applicant has thus shown, unexpectedly and surprisingly, that a combination of at least one prostaglandin receptor agonist and at least one MC1R receptor agonist stimulates melanogenesis. Such a combination appears to be effective for the treatment and/or prevention of dermatological conditions linked to hypopigmentation. Furthermore, this combination limits the risks of side effects regardless of the duration of application of this combination product. In particular, such a product makes it possible to correct hypopigmentations at the skin level by increasing melanogenesis by virtue of a potentiated effect also known as potentiation or synergy.

A method for treating dermatological conditions linked to hypopigmentation, comprising at least one prostaglandin receptor agonist in association or in combination with at least one MC1R receptor agonist, is thus described.

A subject of the invention is a combination product comprising at least one prostaglandin receptor agonist and at least one MC1R receptor agonist, as a medicament for use simultaneously, separately or spread out over time for the treatment and/or prevention of dermatological conditions linked to hypopigmentation.

According to one aspect of the invention, the prostaglandin receptor agonist and the MC1R receptor agonist are present in the same composition.

According to another aspect of the invention, the prostaglandin receptor agonist and the MC1R receptor agonist are present separately from one another in distinct compositions.

Thus, another subject of the invention relates to an administration (or a regimen of administration) of a composition comprising the prostaglandin receptor agonist administered first, and then a composition comprising the MC1R receptor agonist administered second.

According to one aspect of the invention, the prostaglandin receptor agonist is present at a concentration of between approximately 0.001% and 1% by weight, relative to the total weight of the composition comprising it. The MC1R receptor agonist is present at a concentration of between approximately 0.001% and 10% by weight, relative to the total weight of the composition comprising it.

In one preferred aspect of the invention, the combination product comprises at least one prostaglandin receptor agonist at a concentration of between approximately 0.004% and 0.04% and at least one MC1R receptor agonist at a concentration of between approximately 5% and 10% by weight, relative to the total weight of the composition comprising it, as a medicament for use simultaneously, separately or spread out over time for the treatment and/or prevention of dermatological conditions linked to hypopigmentation.

In one preferred aspect of the invention, the composition(s) is (are) administered topically.

According to one particular aspect of the invention, the prostaglandin receptor agonist is a PGE or PGF agonist; preferably, it is a PGF2$\alpha$ agonist and is preferentially chosen from latanoprost, bimatoprost, travoprost, fluprostenol and unoprostone; preferentially travoprost.

According to one particular aspect of the invention, the MC1R receptor agonist is chosen from $\alpha$, $\beta$ or $\gamma$ melanocyte-stimulating hormones (MSH), adrenocorticotropic hormone (ACTH) 1-39, $\beta$-lipotropin, $\beta$-endorphin and compounds of general formula (I) or (II) as subsequently defined.

Another subject of the invention relates to an MC1R receptor agonist for use in the treatment and/or prevention of dermatological conditions linked to hypopigmentation, in association or in combination with at least one prostaglandin receptor agonist, as a medicament for use simultaneously, separately or spread out over time.

Another subject of the invention relates to a composition comprising at least one MC1R receptor agonist and at least one prostaglandin receptor agonist, in a physiologically acceptable carrier.

DETAILED DESCRIPTION

The invention and the ensuing advantages will be understood more clearly upon reading the description and the non-limiting embodiments which follow.

Throughout the present description, unless otherwise specified, it is understood that, when concentration ranges are given, they include the upper and lower limits of said range.

The invention is directed toward the treatment and/or prevention of dermatological conditions linked to hypopigmentation or depigmentation of the skin in a patient.

The patient is defined as a human being, regardless of age.

According to a general definition, the term "treatment" is intended to mean an improvement in or relief for some or all of the major symptoms of the dermatological disease or condition. In particular, the treatment promotes melanogenesis and/or melanocyte migration and/or melanoblast differentiation and/or proliferation.

The term "prevention" is intended to mean the limitation or the prevention of the appearance of the major symptoms of the dermatological condition.

The dermatological condition linked to hypopigmentation which is targeted by the invention is in particular a depigmentation or a hypopigmentation and is preferentially chosen from vitiligo, albinism, hypomelanosis, depigmentations caused by physical or chemical agents, post-inflammatory hypopigmentations, Sutton's phenomenon or any other hypopigmentary lesions, even more preferentially vitiligo.

The term "hypopigmentation" is intended to mean a decrease in the usual coloration of the skin, of body hair or of head hair, or even a total discoloration, resulting in a depigmentation characterized by the absence of melanocytes in the affected area.

The invention comprises the association or the combination of at least one prostaglandin receptor agonist and at least one MC1R receptor agonist.

The prostaglandin receptor agonist according to the invention is preferentially a PGE or PGF agonist, more preferentially a PGE2 and PGF2α agonist, and even more preferentially a PGF2α agonist.

The PGF2α agonist according to the invention is preferentially chosen from latanoprost, bimatoprost, travoprost, fluprostenol and unoprostone, even more preferentially travoprost.

The MC1R receptor agonist according to the invention is preferentially chosen from α, β or γ melanocyte-stimulating hormones (MSH), adrenocorticotropic hormone (ACTH) 1-39, β-lipotropin, β-endorphin and compounds of general formula (I) or (II) below:

in which, for formula (I):

R1 represents a hydrogen atom, an aryl, a substituted aryl, an alkyl, a cycloalkyl, a cycloalkylalkyl, or a cycloalkylalkylalkyl;

R2 represents a hydrogen atom, a hydroxyl, a lower alkyl, a substituted lower alkyl, a higher alkyl, a substituted higher alkyl, a cycloalkyl, a cycloalkylalkyl, a lower alkoxy, a substituted lower alkoxy, a higher alkoxy, a substituted higher alkoxy, a cycloalkylalkoxy, an acyloxy, an acyl, an alkoxycarbonyl, a carboxamide, a carboxylic acid, a cyano, or an amino disubstituted with an acyl and an aryl or alkyl;

R3 represents an aralkyl or a substituted aralkyl;

R4 represents a heteroaralkyl or a substituted heteroaralkyl;

R5 represents a hydrogen atom or an alkyl;

X represents an oxygen atom or a sulfur atom;

n and m may be equal to 1 or 2;

and also the corresponding salts and enantiomers;

in which, for general formula (II):

R1 represents an aryl, a substituted aryl or a cycloalkyl;

R2 represents a hydrogen atom, a hydroxyl, a lower alkyl, a substituted lower alkyl, a higher alkyl, a substituted higher alkyl, a cycloalkyl, a cycloalkylalkyl which may be substituted, a lower alkoxy, a substituted lower alkoxy, a higher alkoxy, a substituted higher alkoxy, a cycloalkylalkoxy, or an acyloxy;

R3 represents an aralkyl or a substituted aralkyl;

R4 represents a heteroaralkyl, a substituted heteroaralkyl, a heteroalkyl or a substituted heteroalkyl;

R5 represents a hydrogen atom, a hydroxyl, an amino, an acylamino or a sulfonamide;

and also the corresponding salts and enantiomers of the compounds of general formula (I).

According to one of the preferred aspects, in general formula (II):

R1 represents a cyclopropylmethyl or a 4-hydroxybutyl group;

R2 represents a hydrogen atom or a methyl group.

Among the addition salts of the compounds of general formula (I) or (II) with a pharmaceutically acceptable acid, mention may preferably be made of the salts with an organic acid or with an inorganic acid.

Suitable inorganic acids are, for example, hydrohalic acids such as hydrochloric acid or hydrobromic acid, sulfuric acid and nitric acid.

Suitable organic acids are, for example, picric acid, methanesulfonic acid, ethanesulfonic acid, para-toluenesulfonic acid, oxalic acid and tartaric acid.

The compounds of general formula (I) or (II) may also exist in the form of hydrates or of solvates with water or with a solvent.

Suitable solvents for forming solvates or hydrates are, for example, alcohols, for instance ethanol or isopropanol, or water.

According to the present invention, an aryl denotes, in particular, a phenyl or a naphthyl which is unsubstituted.

According to the present invention, a substituted aryl denotes, in particular, a phenyl or a naphthyl which is substituted with one or more groups of atoms chosen from an alkyl, an alkoxy, a halogen, a hydroxyl, a cyano, a trifluoromethyl and a nitro.

According to the present invention, a cycloalkyl denotes, in particular, a cyclic, saturated hydrocarbon-based chain comprising from 3 to 7 carbon atoms.

According to the present invention, hydroxyl denotes the OH group.

According to the present invention, amino denotes the $NH_2$ group.

According to the present invention, cyano denotes the CN group.

According to the present invention, a carboxylic acid denotes, in particular, the $CO_2H$ group.

According to the present invention, an acyl denotes, in particular, a formyl or a carbonyl substituted with an alkyl, a cycloalkyl or a cycloalkylalkyl.

According to the present invention, an alkyl denotes, in particular, a substituted or unsubstituted lower alkyl or a substituted or unsubstituted higher alkyl.

According to the present invention, a lower alkyl denotes, in particular, a linear or branched, saturated or unsaturated, hydrocarbon-based chain comprising from 1 to 4 carbon atoms or an unsaturated hydrocarbon-based chain comprising from 2 to 4 carbon atoms and in particular, for example, methyl, ethyl, propyl, isopropyl or butyl.

According to the present invention, a substituted lower alkyl denotes, in particular, a linear or branched, saturated or unsaturated, hydrocarbon-based chain comprising from 1 to 4 carbon atoms and substituted with one or more halogen atoms or with a hydroxyl, or an unsaturated hydrocarbon-based chain comprising from 2 to 4 carbon atoms and substituted with one or more halogen atoms or with a hydroxyl.

According to the present invention, a higher alkyl denotes, in particular, a saturated or unsaturated, linear or branched, hydrocarbon-based chain comprising from 5 to 10 carbon atoms.

According to the present invention, a substituted higher alkyl denotes, in particular, a saturated or unsaturated, linear or branched, hydrocarbon-based chain comprising from 5 to 10 carbon atoms and substituted with one or more halogen atoms or with a hydroxyl.

According to the present invention, a halogen atom denotes, in particular, chlorine, fluorine, iodine and bromine atoms.

According to the present invention, a cycloalkylalkyl denotes, in particular, an alkyl substituted with a cycloalkyl.

According to the present invention, a lower alkoxy denotes, in particular, an oxygen atom substituted with a lower alkyl and in particular, for example, methoxy, ethoxy, propoxy, isopropoxy or butoxy.

According to the present invention, a substituted lower alkoxy denotes, in particular, an oxygen atom substituted with a substituted lower alkyl.

According to the present invention, a higher alkoxy denotes, in particular, an oxygen atom substituted with a higher alkyl.

According to the present invention, a substituted higher alkoxy denotes, in particular, an oxygen atom substituted with a substituted higher alkyl.

According to the present invention, a cycloalkylalkoxy denotes, in particular, an oxygen atom substituted with a cycloalkylalkyl.

According to the present invention, an acyloxy denotes, in particular, an oxygen atom substituted with an acyl.

According to the present invention, an alkoxycarbonyl denotes, in particular, a carbonyl substituted with an alkoxy, a cycloalkoxy or a cycloalkylalkoxy.

According to the present invention, a carboxamide denotes, in particular, a carbonyl substituted with a monoalkylamino or a dialkylamino.

According to the present invention, an aralkyl denotes, in particular, an alkyl substituted with an aryl.

According to the present invention, a substituted aralkyl denotes, in particular, an alkyl substituted with a substituted aryl.

According to the present invention, a heterocycle denotes, in particular, a saturated or unsaturated, cyclic or bicyclic, hydrocarbon-based chain comprising one or more heteroatoms chosen from O, S and N.

According to the present invention, a substituted heterocycle denotes, in particular, a saturated or unsaturated, cyclic or bicyclic, hydrocarbon-based chain comprising one or more heteroatoms chosen from O, S and N, substituted with one or more alkyl groups.

According to the present invention, a heteroaryl denotes, in particular, an aromatic heterocycle.

According to the present invention, a substituted heteroaryl denotes, in particular, an aromatic heterocycle substituted with one or more alkyl groups.

According to the present invention, a heteroaralkyl denotes, in particular, an alkyl substituted with a heteroaryl.

According to the present invention, a substituted heteroaralkyl denotes, in particular, an alkyl substituted with a substituted heteroaryl.

The MC1R receptor agonist according to the invention is more preferentially chosen from the following compounds of general formula (I):

1-[(S)-2-(4-Butyryl-4-phenylpiperidin-1-yl)-1-(4-methoxybenzyl)-2-oxoethyl]-3-[2-(1H-imidazol-4-yl)ethyl]urea;

1-[2-(1H-Imidazol-4-yl)ethyl]-3-[1-(4-methoxybenzyl)-2-oxo-2-(4-oxo-1-phenyl-1,3,8-triazaspiro[4.5]dec-8-yl)ethyl]urea;

1-[2-(4-Cyano-4-phenylpiperidin-1-yl)-1-(4-methoxybenzyl)-2-oxoethyl]-3-[2-(1H-imidazol-4-yl)ethyl]urea;

1-[2-(1H-Imidazol-4-yl)ethyl]-3-[1-(4-methoxybenzyl)-2-oxo-2-(4-phenylpiperidin-1-yl)ethyl]urea;

1-[2-(1H-Imidazol-4-yl)ethyl]-3-[1-(4-methoxybenzyl)-2-oxo-2-piperidin-1-ylethyl]urea;

Ethyl 4-cyclohexyl-1-[2-{3-[2-(1H-imidazol-4-yl)ethyl]ureido}-3-(4-methoxyphenyl)propionyl]piperidine-4-carboxylate;

N-{1-[2-{3-[2-(1H-Imidazol-4-yl)ethyl]ureido}-3-(4-methoxyphenyl)propionyl]piperidin-4-yl}-N-phenylpropionamide;

1-[2-{3-[2-(1H-Imidazol-4-yl)ethyl]ureido}-3-(4-methoxyphenyl)propionyl]-3-phenylazetidin-3-yl butyrate;

Ethyl 1-[2-{3-[2-(1H-imidazol-4-yl)ethyl]ureido}-3-(4-methoxyphenyl)propionyl]piperidine-4-carboxylate;

1-[2-(1H-Imidazol-4-yl)ethyl]-3-{1-(4-methoxybenzyl)-2-[4-(2-methoxyphenyl)piperidin-1-yl]-2-oxoethyl}urea;

1-[2-(3-Butoxy-3-phenylazetidin-1-yl)-1-(4-methoxybenzyl)-2-oxoethyl]-3-[2-(1H-imidazol-4-yl)ethyl]urea;

Methyl 4-cyclohexyl-1-[2-{3-[2-(1H-imidazol-4-yl)ethyl]ureido}-3-(4-methoxyphenyl)propionyl]piperidine-4-carboxylamide;

1-[2-(3-Cyclohexanecarbonylazetidin-1-yl)-1-(4-methoxybenzyl)-2-oxoethyl]-3-[2-(1H-imidazol-4-yl)ethyl]urea;

Ethyl 4-cyclohexyl-1-[2-{3-ethyl-3-[2-(1H-imidazol-4-yl)ethyl]ureido}-3-(4-methoxyphenyl)propionyl]piperidine-4-carboxylate;

N-Cyclopropyl-N-{1-[2-{3-[2-(1H-imidazol-4-yl)ethyl]ureido}-3-(4-methoxyphenyl)propionyl]piperidin-4-yl}propionamide;

Ethyl 4-cyclohexyl-1-(2-{3-[2-(1H-imidazol-4-yl)ethyl]ureido}-3-phenylpropionyl)piperidine-4-carboxylate;

1-[2-(4-Butyryl-4-cyclohexylpiperidin-1-yl)-1-(4-methoxybenzyl)-2-oxoethyl]-3-[2-(3H-imidazol-4-yl)ethyl]urea;

1-[2-(4-Butoxy-4-cyclohexylpiperidin-1-yl)-1-(4-methoxybenzyl)-2-oxoethyl]-3-[2-(1H-imidazol-4-yl)ethyl]urea;

Ethyl 4-cyclohexyl-1-(2-{3-[2-(1H-imidazol-4-yl)ethyl]ureido}-2-phenylacetyl)piperidine-4-carboxylate;

Methyl 4-cyclohexyl-1-[2-{3-[2-(1H-imidazol-4-yl)ethyl]ureido}-3-(4-methoxyphenyl)propionyl]piperidine-4-carboxylate;

1-[2-(4-Cyclohexyl-4-ethoxypiperidin-1-yl)-1-(4-methoxybenzyl)-2-oxoethyl]-3-[2-(1H-imidazol-4-yl)ethyl]urea;

1-[2-(4-Acetyl-4-cyclohexylpiperidin-1-yl)-1-(4-methoxybenzyl)-2-oxoethyl]-3-[2-(1H-imidazol-4-yl)ethyl]urea;
Methyl 4-cyclohexyl-1-(2-{3-[2-(1H-imidazol-4-yl)ethyl]ureido}-2-phenylacetyl)piperidine-4-carboxylate;
Ethyl 4-ethyl-1-[2-{3-[2-(1H-imidazol-4-yl)ethyl]ureido}-3-(4-methoxyphenyl)propionyl]piperidine-4-carboxylate;
1-[2-(4-Cyclohexyl-4-propoxypiperidin-1-yl)-1-(4-methoxybenzyl)-2-oxoethyl]-3-[2-(1H-imidazol-4-yl)ethyl]urea;
4-Cyclohexyl-1-[2-{3-[2-(1H-imidazol-4-yl)ethyl]ureido}-3-(4-methoxyphenyl)propionyl]piperidine-4-carboxylic acid;
1-[2-(1H-Imidazol-4-yl)ethyl]-3-{1-(4-methoxybenzyl)-2-[3-(2-methyl cyclohexyl)-3-propoxyazetidin-1-yl]-2-oxoethyl}urea;
Propyl 4-cyclohexyl-1-[2-{3-[2-(1H-imidazol-4-yl)ethyl]ureido}-3-(4-methoxyphenyl)propionyl]piperidine-4-carboxylate;
1-[2-(1H-Imidazol-4-yl)ethyl]-3-[1-(4-methoxybenzyl)-2-oxo-2-(3-pentyl-3-phenylazetidin-1-yl)ethyl]urea;
Ethyl 1-((R)-3-(4-chlorophenyl)-2-{3-[2-(1H-imidazol-4-yl)ethyl]ureido}propionyl)-4-cyclohexylpiperidine-4-carboxylate;
Ethyl 1-((S)-3-(4-chlorophenyl)-2-{3-[2-(1H-imidazol-4-yl)ethyl]ureido}propionyl)-4-cyclohexylpiperidine-4-carboxylate;
1-[2-(4-Cyclohexyl-4-propionylpiperidin-1-yl)-1-(4-methoxybenzyl)-2-oxoethyl]-3-[2-(1H-imidazol-4-yl)ethyl]urea;
1-[2-(4-Cyclohexyl-4-propionylpiperidin-1-yl)-1-(4-methoxybenzyl)-2-oxoethyl]-3-(1H-imidazol-4-ylmethyl)urea;
Ethyl 4-cyclohexyl-1-[(R)-2-{3-[2-(1H-imidazol-4-yl)ethyl]ureido}-3-(4-methoxyphenyl)propionyl]piperidine-4-carboxylate;
Ethyl 4-cyclopropylmethyl-1-[2-{3-[2-(1H-imidazol-4-yl)ethyl]ureido}-3-(4-methoxyphenyl)propionyl]piperidine-4-carboxylate;
Propyl 4-cyclohexyl-1-(2-{3-[2-(1H-imidazol-4-yl)ethyl]ureido}-3-phenylpropionyl)piperidine-4-carboxylate;
Ethyl 4-cyclopentyl-1-(2-{3-[2-(1H-imidazol-4-yl)ethyl]ureido}-3-phenylpropionyl)piperidine-4-carboxylate;
Ethyl 4-cyclopentyl-1-[2-{3-[2-(1H-imidazol-4-yl)ethyl]ureido}-3-(4-methoxyphenyl)propionyl]piperidine-4-carboxylate;
Ethyl 4-cyclohexyl-1-[(S)-2-{3-[2-(1H-imidazol-4-yl)ethyl]ureido}-3-(4-methoxyphenyl)propionyl]piperidine-4-carboxylate;
1-[(R)-2-(4-Butyryl-4-cyclohexylpiperidin-1-yl)-1-(4-methoxybenzyl)-2-oxoethyl]-3-[2-(1H-imidazol-4-yl)ethyl]urea;
1-[(R)-2-(4-Butyryl-4-cyclohexylpiperidin-1-yl)-1-(4-fluorobenzyl)-2-oxoethyl]-3-[2-(1H-imidazol-4-yl)ethyl]urea;
1-[(R)-1-Benzyl-2-(4-butyryl-4-cyclohexylpiperidin-1-yl)-2-oxoethyl]-3-[2-(1H-imidazol-4-yl)ethyl]urea;
1-[(R)-2-(4-Butyryl-4-cyclohexylpiperidin-1-yl)-1-(4-methoxybenzyl)-2-oxoethyl]-3-[2-(3-methyl-3H-imidazol-4-yl)ethyl]urea;
1-[(R)-2-(4-Butyryl-4-cyclohexylpiperidin-1-yl)-1-(4-chlorobenzyl)-2-oxoethyl]-3-[2-(1H-imidazol-4-yl)ethyl]urea;
Ethyl 4-cyclohexyl-1-((R)-3-(3,4-dichlorophenyl)-2-{3-[3-(1H-imidazol-4-yl)propyl]ureido}propionyl)piperidine-4-carboxylate;
Ethyl 4-cyclohexyl-1-((R)-3-(4-methoxyphenyl)-2-{3-[2-(3-methyl-3H-imidazol-4-yl)ethyl]ureido}propionyl)piperidine-4-carboxylate;
Ethyl 4-cyclohexyl-1-[(R)-2-{3-[2-(1H-imidazol-4-yl)ethyl]thioureido}-3-(4-methoxyphenyl)propionyl]piperidine-4-carboxylate;
1-[(R)-2-(4-Butyryl-4-cyclohexylpiperidin-1-yl)-1-(4-methoxybenzyl)-2-oxoethyl]-3-[2-(1H-imidazol-4-yl)ethyl]thiourea;
1-[(R)-2-(4-Cyclohexyl-4-propoxypiperidin-1-yl)-1-(4-methoxybenzyl)-2-oxoethyl]-3-[2-(1H-imidazol-4-yl)ethyl]thiourea;
1-[(R)-1-Benzyl-2-(4-cyclohexyl-4-propoxypiperidin-1-yl)-2-oxoethyl]-3-[2-(1H-imidazol-4-yl)ethyl]thiourea;
1-[(R)-1-Benzyl-2-(4-cyclohexyl-4-propoxypiperidin-1-yl)-2-oxoethyl]-3-[2-(1H-imidazol-4-yl)ethyl]urea;
Ethyl 4-cyclohexyl-1-((R)-3-(4-methoxyphenyl)-2-{3-[2-(3-methyl-3H-imidazol-4-yl)ethyl]thioureido}propionyl)piperidine-4-carboxylate;
Ethyl 4-cyclohexyl-1-((R)-2-{3-[2-(3-methyl-3H-imidazol-4-yl)ethyl]ureido}-3-phenylpropionyl)piperidine-4-carboxylate;
1-[(R)-2-(4-Cyclohexyl-4-propoxypiperidin-1-yl)-1-(4-methoxybenzyl)-2-oxoethyl]-3-[2-(3-methyl-3H-imidazol-4-yl)ethyl]urea;
Ethyl 1-((R)-3-(4-chlorophenyl)-2-{3-[2-(3-methyl-3H-imidazol-4-yl)ethyl]ureido}propionyl)-4-cyclohexylpiperidine-4-carboxylate;
Ethyl 4-cyclohexyl-1-((R)-3-(4-fluorophenyl)-2-{3-[2-(3-methyl-3H-imidazol-4-yl)ethyl]ureido}propionyl)piperidine-4-carboxylate;
Ethyl 4-cyclohexyl-1-((R)-3-(4-fluorophenyl)-2-{3-[2-(1H-imidazol-4-yl)ethyl]ureido}propionyl)piperidine-4-carboxylate;
Ethyl 4-cyclohexyl-1-((R)-3-(4-fluorophenyl)-2-{3-[2-(1H-imidazol-4-yl)ethyl]thioureido}propionyl)piperidine-4-carboxylate;
Ethyl 1-((R)-3-(4-chlorophenyl)-2-{3-[2-(1H-imidazol-4-yl)ethyl]thioureido}propionyl)-4-cyclohexylpiperidine-4-carboxylate;
Ethyl 1-((R)-3-(4-chlorophenyl)-2-{3-[2-(3-methyl-3H-imidazol-4-yl)ethyl]thioureido}propionyl)-4-cyclohexylpiperidine-4-carboxylate;
1-[(R)-2-(4-Cyclohexyl-4-propoxypiperidin-1-yl)-1-(4-fluorobenzyl)-2-oxoethyl]-3-[2-(1H-imidazol-4-yl)ethyl]urea;
1-[(R)-1-(4-Chlorobenzyl)-2-(4-cyclohexyl-4-propoxypiperidin-1-yl)-2-oxoethyl]-3-[2-(1H-imidazol-4-yl)ethyl]urea; and also the respective salts and enantiomers thereof.

The MC1R agonist according to the invention is even more preferentially ethyl 4-cyclohexyl-1-[(R)-2-{3-[2-(1H-imidazol-4-yl)ethyl]ureido}-3-(4-methoxyphenyl)propionyl]piperidine-4-carboxylate.

The MC1R receptor agonist according to the invention is more preferentially chosen from the following compounds of general formula (II):

1-[(S)-2-[(S)-2-Benzoylamino-3-(1H-imidazol-4-yl)propionylamino]-3-(4-methoxyphenyl)propionyl]-3-phenylazetidin-3-yl butyric acid ester
N-[(S)-1-[(S)-2-(3-Butoxy-3-o-tolylazetidin-1-yl)-1-(4-methoxybenzyl)-2-oxoethylcarbamoyl]-2-(1H-imidazol-4-yl)ethyl]benzamide
N-[(S)-1-[(S)-2-(3-Butoxy-3-phenylazetidin-1-yl)-1-(4-methoxybenzyl)-2-oxoethylcarbamoyl]-2-(1H-imidazol-4-yl)ethyl]benzamide N-[(S)-1-[(S)-2-(3-Hydroxy-3-o-tolylazetidin-1-yl)-1-(4-methoxybenzyl)-2-oxoethylcarbamoyl]-2-(1H-imidazol-4-yl)ethyl]benzamide 1-[(S)-2-[(S)-2-Benzoylamino-3-(1H-imidazol-4-yl)propionylamino]-3-(4-methoxyphenyl)propionyl]-3-o-tolylazetidin-3-yl acetate Butyric acid 1-[(S)-2-[(S)-2-benzoylamino-3-(1H-imidazol-4-yl)propionylamino]-3-(4-methoxyphenyl)propionyl]-3-(4-fluorophenyl)azetidin-3-yl ester N-[(S)-1-[(S)-2-(3-Cyclohexyl-3-hydroxyazetidin-1-yl)-1-(4-methoxybenzyl)-2-oxoethylcarbamoyl]-2-(1H-imidazol-4-yl)ethyl]benzamide N-[(S)-1-[(S)-2-[3-Butoxy-3-(4-fluorophenyl)azetidin-1-yl]-1-(4-methoxybenzyl)-2-oxoethylcarbamoyl]-2-(1H-imidazol-4-yl)ethyl]benzamide N-[(S)-1-[(S)-2-[3-Butoxy-3-(3-fluorophenyl)azetidin-1-yl]-1-(4-methoxybenzyl)-2-oxoethylcarbamoyl]-2-(1H-imidazol-4-yl)ethyl]benzamide N-[(S)-2-(3-Cyclohexyl-3-hydroxyazetidin-1-yl)-1-(4-methoxybenzyl)-2-oxoethyl]-3-(1H-imidazol-4-yl)propionamide N-[(S)-2-(3-Hydroxy-3-o-tolylazetidin-1-yl)-1-(4-methoxybenzyl)-2-oxoethyl]-3-(1H-imidazol-4-yl)propionamide N-[(R)-1-(3,4-Dichlorobenzyl)-2-(3-hydroxy-3-phenylazetidin-1-yl)-2-oxoethyl]-3-(1H-imidazol-4-yl)propionamide N-[(S)-2-(3-Ethoxy-3-o-tolylazetidin-1-yl)-1-(4-methoxybenzyl)-2-oxoethyl]-3-(1H-imidazol-4-yl)propionamide N-[(S)-2-(3-Cyclopropylmethoxy-3-o-tolylazetidin-1-yl)-1-(4-methoxybenzyl)-2-oxoethyl]-3-(1H-imidazol-4-yl)propionamide N-[(R)-2-(3-Butoxy-3-o-tolylazetidin-1-yl)-1-(4-methoxybenzyl)-2-oxoethyl]-3-(1H-imidazol-4-yl)propionamide N-[(S)-2-(3-Butoxy-3-o-tolylazetidin-1-yl)-1-(4-methoxybenzyl)-2-oxoethyl]-3-(1H-imidazol-4-yl)propionamide N-[(R)-2-(3-Ethoxy-3-o-tolylazetidin-1-yl)-1-(4-methoxybenzyl)-2-oxoethyl]-3-(1H-imidazol-4-yl)propionamide N-[(R)-2-(3-Butoxy-3-phenylazetidin-1-yl)-1-cyclohexylmethyl-2-oxoethyl]-3-(1H-imidazol-4-yl)propionamide N-[(R)-2-(3-Butoxy-3-phenylazetidin-1-yl)-1-(2,4-dichlorobenzyl)-2-oxoethyl]-3-(1H-imidazol-4-yl)propionamide N-[(R)-2-(3-Cyclopropylmethoxy-3-o-tolylazetidin-1-yl)-1-(4-methoxybenzyl)-2-oxoethyl]-3-(1H-imidazol-4-yl)propionamide N-[(S)-1-(4-Methoxybenzyl)-2-oxo-2-(3-propoxy-3-o-tolylazetidin-1-yl)ethyl]-3-(1H-imidazol-4-yl)propionamide N-[(R)-1-(4-Methoxybenzyl)-2-oxo-2-(3-propoxy-3-o-tolylazetidin-1-yl)ethyl]-3-(1H-imidazol-4-yl)propionamide N-[(R)-2-[3-Butoxy-3-(4-fluorophenyl)azetidin-1-yl]-1-(4-methoxybenzyl)-2-oxoethyl]-3-(1H-imidazol-4-yl)propionamide N-[(R)-1-(4-Methoxybenzyl)-2-oxo-2-(3-pentyloxy-3-o-tolylazetidin-1-yl)ethyl]-3-(1H-imidazol-4-yl)propionamide N-[(R)-2-(3-Hexyloxy-3-o-tolylazetidin-1-yl)-1-(4-methoxybenzyl)-2-oxoethyl]-3-(1H-imidazol-4-yl)propionamide N-[(R)-1-(4-Methoxybenzyl)-2-oxo-2-(3-pentyl-3-phenylazetidin-1-yl)ethyl]-3-(1H-imidazol-4-yl)propionamide N-[(R)-2-(3-Butyl-3-phenylazetidin-1-yl)-1-(4-methoxybenzyl)-2-oxoethyl]-3-(1H-imidazol-4-yl)propionamide N-[(R)-2-(3-Cyclopropylmethoxy-3-phenylazetidin-1-yl)-1-(4-methoxybenzyl)-2-oxo-ethyl]-3-(1H-imidazol-4-yl)propionamide N-[(R)-2-(3-Hydroxy-3-o-tolylazetidin-1-yl)-1-(4-methoxybenzyl)-2-oxoethyl]-3-(1H-imidazol-4-yl)propionamide N-[(R)-2-[3-Butoxy-3-(4-fluorophenyl)azetidin-1-yl]-1-(3-fluorobenzyl)-2-oxoethyl]-3-(1H-imidazol-4-yl)propionamide N-[(R)-2-[3-Butoxy-3-(4-fluorophenyl)azetidin-1-yl]-1-(4-fluorobenzyl)-2-oxoethyl]-3-(1H-imidazol-4-yl)propionamide N-[(R)-2-(3-Butoxy-3-phenylazetidin-1-yl)-1-(4-fluorobenzyl)-2-oxoethyl]-3-(1H-imidazol-4-yl)propionamide N-{(R)-1-Benzyl-2-[3-butoxy-3-(4-fluorophenyl)azetidin-1-yl]-2-oxoethyl}-3-(4H-imidazol-2-yl)propionamide N-[(R)-1-Benzyl-2-(3-butoxy-3-phenylazetidin-1-yl)-2-oxoethyl]-3-(1H-imidazol-4-yl)propionamide N-[(R)-2-(3-Butoxy-3-phenylazetidin-1-yl)-1-(4-methoxybenzyl)-2-oxoethyl]-3-(1H-imidazol-4-yl)propionamide N-[(R)-1-(4-Methoxybenzyl)-2-oxo-2-(3-pentyl-3-o-tolylazetidin-1-yl)ethyl]-3-(1H-imidazol-4-yl)propionamide N-[(R)-2-[3-(4-Fluorophenyl)-3-pentylazetidin-1-yl]-1-(4-methoxybenzyl)-2-oxoethyl]-3-(1H-imidazol-4-yl)propionamide N-[(R)-2-(3-Butoxy-3-o-tolylazetidin-1-yl)-1-(4-methoxybenzyl)-2-oxoethyl]-3-(1H-[1,2,3]triazol-4-yl)propionamide N-[(R)-2-(3-Butoxy-3-o-tolylazetidin-1-yl)-1-(4-methoxybenzyl)-2-oxoethyl]-3-(5-methyl-3H-[1,2,4]triazol-3-yl)propionamide N-[(R)-2-(3-Butoxy-3-o-tolylazetidin-1-yl)-1-(4-methoxybenzyl)-2-oxoethyl]-3-(5-methyl-3H-imidazol-4-yl)propionamide N-{(R)-1-(4-Methoxybenzyl)-2-[3-(2-methoxyphenyl)-3-pentylazetidin-1-yl]-2-oxoethyl}-3-(1H-imidazol-4-yl)propionamide N-[(R)-2-[3-(2-Fluorophenyl)-3-pentylazetidin-1-yl]-1-(4-methoxybenzyl)-2-oxoethyl]-3-(1H-imidazol-4-yl)propionamide N-[(R)-2-[3-(2-Chlorophenyl)-3-pentylazetidin-1-yl]-1-(4-methoxybenzyl)-2-oxoethyl]-3-(1H-imidazol-4-yl)propionamide N-[(R)-1-(4-Chlorobenzyl)-2-oxo-2-(3-pentyl-3-phenylazetidin-1-yl)ethyl]-3-(1H-imidazol-4-yl)propionamide N-[(R)-1-(4-Fluorobenzyl)-2-oxo-2-(3-pentyl-3-phenylazetidin-1-yl)ethyl]-3-(1H-imidazol-4-yl)propionamide N-[(R)-1-Benzyl-2-oxo-2-(3-pentyl-3-phenylazetidin-1-yl)ethyl]-3-(1H-imidazol-4-yl)propionamide N-[(R)-2-(3-Butoxy-3-o-tolylazetidin-1-yl)-1-(4-methoxybenzyl)-2-oxoethyl]-3-(1H-imidazol-4-yl)acrylamide N-[(R)-2-[3-(2,4-Difluorophenyl)-3-pentylazetidin-1-yl]-1-(4-methoxybenzyl)-2-oxoethyl]-3-(1H-imidazol-4-yl)propionamide N-[(R)-2-Oxo-2-(3-pentyl-3-phenylazetidin-1-yl)-1-(3-trifluoromethylbenzyl)ethyl]-3-(1H-imidazol-4-yl)propionamide N-[(R)-2-Oxo-2-(3-pentyl-3-phenylazetidin-1-yl)-1-(4-trifluoromethylbenzyl)ethyl]-3-(1H-imidazol-4-yl)propionamide N-[(R)-1-(3,4-Dichlorobenzyl)-2-oxo-2-(3-pentyl-3-phenylazetidin-1-yl)ethyl]-3-(1H-imidazol-4-yl)propionamide N-[(R)-1-(3,4-Difluorobenzyl)-2-oxo-2-(3-pentyl-3-phenylazetidin-1-yl)-ethyl]-3-(1H-imidazol-4-yl)propionamide N-[(R)-2-[3-(3,4-Dichlorophenyl)-3-pentylazetidin-1-yl]-1-(4-methoxybenzyl)-2-oxoethyl]-3-(1H-imidazol-4-yl)propionamide N-[(R)-2-[3-(3-Fluorophenyl)-3-pentylazetidin-1-yl]-1-(4-methoxybenzyl)-2-oxoethyl]-3-(1H-imidazol-4-yl)propionamide N-[(R)-1-(3-Fluorobenzyl)-2-oxo-2-(3-pentyl-3-phenylazetidin-1-yl)ethyl]-3-(1H-imidazol-4-yl)propionamide
N-[(R)-1-(2-Fluorobenzyl)-2-oxo-2-(3-pentyl-3-phenylazetidin-1-yl)ethyl]-3-(1H-imidazol-4-yl)propionamide
N-[(R)-1-(2,4-Dichlorobenzyl)-2-oxo-2-(3-pentyl-3-phenylazetidin-1-yl)ethyl]-3-(1H-imidazol-4-yl)propionamide
N-[(R)-2-[3-(4-Chlorophenyl)-3-pentylazetidin-1-yl]-1-(4-methoxybenzyl)-2-oxoethyl]-3-(1H-imidazol-4-yl)propionamide
N-[(R)-2-[3-(2,5-Difluorophenyl)-3-pentylazetidin-1-yl]-1-(4-methoxybenzyl)-2-oxoethyl]-3-(1H-imidazol-4-yl)propionamide
N-[(R)-2-[3-(2,6-Difluorophenyl)-3-pentylazetidin-1-yl]-1-(4-methoxybenzyl)-2-oxoethyl]-3-(1H-imidazol-4-yl)propionamide
N-[2-(3-Butoxy-3-o-tolylazetidin-1-yl)-1-(4-methoxybenzyl)-2-oxoethyl]-3-(1H-imidazol-4-yl)hexyramide
N-[2-(3-Butoxy-3-o-tolylazetidin-1-yl)-1-(4-methoxybenzyl)-2-oxoethyl]-3-(1H-imidazol-4-yl)pentyramide
N-[(R)-1-(4-Methoxybenzyl)-2-oxo-2-(3-pentyl-3-phenylazetidin-1-yl)ethyl]-3-(3-methyl-3H-imidazol-4-yl)propionamide
N-[2-(3-Butoxy-3-o-tolylazetidin-1-yl)-1-(2,4-dichlorobenzyl)-2-oxoethyl]-3-(1H-imidazol-4-yl)hexyramide
N-[(R)-2-(3-Cyclohexyl-3-pentylazetidin-1-yl)-1-(4-methoxybenzyl)-2-oxoethyl]-3-(1H-imidazol-4-yl)propionamide
N-[(R)-2-(3-Butoxy-3-o-tolylazetidin-1-yl)-1-(4-methoxybenzyl)-2-oxoethyl]-3-(3-methyl-3H-imidazol-4-yl)propionamide
3-(1H-Imidazol-4-yl)-N-[(R)-1-(4-methoxybenzyl)-2-oxo-2-(3-phenylazetidin-1-yl)ethyl]propionamide
N-[(R)-2-[3-(4-Fluorophenyl)azetidin-1-yl]-1-(4-methoxybenzyl)-2-oxoethyl]-3-(1H-imidazol-4-yl)propionamide
3-(1H-Imidazol-4-yl)-N-{(R)-1-(4-methoxybenzyl)-2-[3-(2-methoxyphenyl)azetidin-1-yl]-2-oxoethyl}propionamide
N-[(R)-2-[3-(2-Fluorophenyl)azetidin-1-yl]-1-(4-methoxybenzyl)-2-oxoethyl]-3-(1H-imidazol-4-yl)propionamide
3-(1H-Imidazol-4-yl)-N-{(R)-1-(4-methoxybenzyl)-2-oxo-2-[3-phenyl-3-(4,4,4-trifluorobutyl)azetidin-1-yl]ethyl}propionamide
N-[(R)-2-[3-(5-Fluoropentyl)-3-phenylazetidin-1-yl]-1-(4-methoxybenzyl)-2-oxoethyl]-3-(1H-imidazol-4-yl)propionamide
N-[(R)-2-(3-Cyclopropyl-3-phenylazetidin-1-yl)-1-(4-methoxybenzyl)-2-oxoethyl]-3-(1H-imidazol-4-yl)propionamide
N-[(R)-2-(3-Cyclopropylmethyl-3-phenylazetidin-1-yl)-1-(4-methoxybenzyl)-2-oxoethyl]-3-(1H-imidazol-4-yl)propionamide
(S)-2-Hydroxy-3-(1H-imidazol-4-yl)-N-[1-(4-methoxybenzyl)-2-oxo-2-(3-propoxy-3-o-tolylazetidin-1-yl)ethyl]propionamide
(S)-2-Amino-3-(1H-imidazol-4-yl)-N-[1-(4-methoxybenzyl)-2-oxo-2-(3-propoxy-3-o-tolylazetidin-1-yl)ethyl]propionamide
N-[2-(3-Butoxy-3-o-tolylazetidin-1-yl)-1-(4-methoxybenzyl)-2-oxoethyl]-3-(1H-imidazol-4-yl)butyramide
(S)-N-[2-(3-Butoxy-3-phenylazetidin-1-yl)-1-(4-methoxybenzyl)-2-oxoethyl]-3-(1H-imidazol-4-yl)-2-methanesulfonylaminopropionamide
N-[(R)-1-(4-Methoxybenzyl)-2-oxo-2-(3-pentyl-3-phenylazetidin-1-yl)ethyl]-3-(1-methyl-1H-imidazol-4-yl)propionamide
N-[(R)-2-[3-(4-Hydroxybutoxy)-3-o-tolylazetidin-1-yl]-1-(4-methoxybenzyl)-2-oxoethyl]-3-(-1H-imidazol-4-yl)propionamide
N-[(R)-2-(3-Cyclopropylmethoxy-3-o-tolylazetidin-1-yl)-1-(4-methoxybenzyl)-2-oxoethyl]-3-(5-methyl-1H-imidazol-4-yl)propionamide and also the corresponding salts and enantiomers thereof.

According to one of the preferred aspects of the invention, the following compounds of formula (II) are also chosen:

N-[(R)-2-[3-(4-Hydroxybutoxy)-3-o-tolylazetidin-1-yl]-1-(4-methoxybenzyl)-2-oxoethyl]-3-(-1H-imidazol-4-yl)propionamide
N-[(R)-2-(3-Cyclopropylmethoxy-3-o-tolylazetidin-1-yl)-1-(4-methoxybenzyl)-2-oxoethyl]-3-(5-methyl-1H-imidazol-4-yl)propionamide and also the corresponding salts and enantiomers.

In the context of the present invention, a combination product comprising a prostaglandin receptor agonist and an MC1R receptor agonist signifies that said combined compounds may be either present in the same composition (defined as a combination or fixed combination), or present separately from one another in distinct compositions. In other words, these compounds are intended to be administered in the context of the same treatment, i.e. over a common treatment period, either at the same time, while optionally being included in one and the same composition, or at different moments. Furthermore, they may be administered via identical or different administration modes and/or may be included in identical or different compositions.

A use simultaneously according to the invention is an administration of the compounds of the product according to the invention included in one and the same pharmaceutical composition.

A use separately according to the invention is an administration, at the same time, of the two compounds of the product according to the invention, each included in a distinct pharmaceutical composition, in an identical or different formulation.

A use spread out over time according to the invention is a successive administration of the two compounds of the product according to the invention, each in a distinct pharmaceutical composition, in an identical or different formulation.

In general, the product according to the invention increases the effectiveness of the prevention and treatment of a dermatological disorder linked to hypopigmentation by increasing melanogenesis. In the context of the invention, the increase in melanogenesis is characterized by an immediate response and a later response through stimulation of the natural pigmentation pathways and an increase in the activity of these pathways.

According to one embodiment of the invention, the administration of a product according to the invention comprising at least the prostaglandin receptor agonist and at least the MC1R receptor agonist in the same composition allows an immediate, simultaneous and complementary action on the melanocytes of the hypopigmented area to be treated and/or close to this area, and in the cases of depigmentation, on the melanocytes of the area surrounding the depigmented area to be treated, so as to stimulate melanogenesis.

The applicant has discovered, unexpectedly and as illustrated in the example, that the prostaglandin receptor agonist which acts immediately (immediate action as defined above) by increasing pheomelanin synthesis in particular, also makes it possible to potentiate the action of the MC1R receptor agonist. Indeed, in vitiligo, a depigmentation which results from the disappearance of the melanocytes in the depigmented lesional areas is observed. The applicant has shown that the prostaglandin receptor agonist compound makes it possible to stimulate the stem cells present at the basal level and activates the differentiation thereof into melanocytes in the lesional areas devoid of melanocytes. This differentiation then allows induction of the expression of the MC1R receptor on the melanocytes. Thus, by revealing MC1R receptor expression on the stem cells, the administration, first, of the prostaglandin receptor agonist will potentiate the effect of the MC1R receptor agonist when it is administered second. The MC1R receptor agonist compound then acts on the newly formed melanocyte MC1R receptors, causing a significant stimulation of tyrosinase activity and of eumelanin synthesis. Furthermore, the administration of an MC1R agonist advantageously increases the MC1R mRNA levels in melanocytes, causing an increase in MC1R expression at the surface of the melanocytes, so as to offer a greater response to hypopigmentation or even depigmentation.

According to one advantageous embodiment of the invention, when a product according to the invention which has the prostaglandin receptor agonist and the MC1R receptor agonist in two distinct compositions is administered, the administration of these compositions, at the same time, makes it possible to obtain an action which is immediate (as defined above) and complementary over time, on the melanocytes, while at the same time also avoiding any possible interaction between these two compounds in a single composition.

Even more advantageously according to the invention, the composition comprising the prostaglandin receptor agonist is administered first, and then the composition comprising the MC1R receptor agonist is administered second.

Furthermore, taking these compositions in a manner separated over time may make it possible to adjust the treatment dosage according to the condition to be treated. For example, taking the composition comprising the prostaglandin receptor agonist first and then taking the composition comprising the MC1R receptor agonist second after a delay in time provides an additional and synergistic effect of the two compounds on the area to be treated and on the surrounding area, more particularly on the melanocytes initially present or generated by the treatment, characterized by a more effective repigmentation of this area.

According to one example of implementation of the invention, when the compounds are present in the same composition for the purpose of administration simultaneously, or when the compounds are present in distinct compositions for the purpose of administration separately, at the same time, the composition(s) is (are) applied every day.

According to the embodiment where the compounds are present in the same composition, said composition is a fixed combination and comprises, in the same physiologically acceptable carrier, (i) at least one prostaglandin receptor agonist and (ii) at least one compound chosen from the MC1R receptor agonist and pharmaceutically acceptable salts or bases thereof. Preferably, the composition is intended for a single topical application per day.

The term "physiologically acceptable carrier" is intended to mean a formulation support which is compatible with the skin and the skin appendages.

The term "fixed combination" should be understood to mean a combination in which the active ingredients are combined at fixed doses in one and the same carrier (single formula) delivering them together at the point of application.

According to another example of implementation of the invention, when the compounds are administered in distinct compositions for the purpose of administration spread out over time, the administration regimen for the composition comprising the prostaglandin receptor agonist and for the composition comprising the MC1R receptor agonist may be variable. Preferentially the composition comprising the prostaglandin receptor agonist is administered before the treatment with the composition comprising the MC1R receptor agonist as illustrated in the example. According to one preferred embodiment, it is administered on the lesioned areas for several consecutive days or even several weeks, and then the composition comprising the MC1R receptor agonist is in turn applied to the lesioned areas for several days or even several weeks.

The practitioner will take care to adjust the duration of the treatment according to the dermatological condition linked to hypopigmentation to be treated and according to the desired result, it being possible for the treatment to be spread out over several months.

Advantageously, the product according to the invention comprises the prostaglandin receptor agonist at a concentration of between approximately 0.001% and 1% by weight, in particular 0.004%, 0.005%, 0.01%, 0.03%, 0.04%, 0.05%, 0.1%, 0.2%, 0.5%, preferably between 0.005% and 0.1%, particularly preferably 0.01% by weight, relative to the total weight of the composition comprising it.

The MC1R receptor agonist at a concentration between approximately 0.001% and 15%, preferably between 0.001% and 10% by weight, preferably between 0.005% and 5%, particularly preferably 5% by weight, but also preferentially between 0.01% and 9%, more preferentially between 0.1% and 8%, and in particular at approximately 0.005%, 0.01%, 0.05%, 0.1%, 0.5%, 1%, 5%, 6%, 7%, 8%, 9% and 10%, by weight, relative to the total weight of the composition comprising it.

According to one particular aspect of the invention, the concentration of the prostaglandin receptor agonist at a concentration of between approximately 0.004% and 0.04% and the concentration of the MC1R receptor agonist at a concentration of between approximately 5% and 10% by weight relative to the total weight of the composition comprising it. More preferentially, the concentration of the prostaglandin receptor agonist at a concentration of between approximately 0.01% and 0.04% and the concentration of the MC1R receptor agonist at a concentration of between approximately 5% and 8% by weight relative to the total weight of the composition.

Thus, according to this particular aspect, the invention relates to a combination product comprising at least one prostaglandin receptor agonist at a concentration of between approximately 0.004% and 0.04% and at least one MC1R receptor agonist at a concentration of between approximately 5% and 10% by weight, relative to the total weight of the composition comprising it, as a medicament for use simultaneously, separately or spread out over time for the treatment and/or prevention of dermatological conditions linked to hypopigmentation.

The present invention therefore relates to a combination product as a medicament intended to be applied topically or systemically, preferably orally, the composition(s) being administered topically or orally, preferentially topically.

When administered orally, the composition(s) may be in the form of tablets, gel capsules, draées, syrups, suspensions, solutions, powders, granules, emulsions, suspensions of microspheres or nanospheres or lipid or polymeric vesicles for controlled release.

When administered topically, the composition(s) according to the invention is (are) preferably in the form of salves, creams, milks, ointments, powders, impregnated pads, syndets, solutions, gels, sprays, foams, suspensions, sticks, shampoos, washing bases or else suspensions of microspheres, nanospheres or lipid or polymeric vesicles, or polymeric or gelled patches for controlled release.

The compositions of the invention also comprise a pharmaceutically acceptable carrier, i.e. a carrier suitable for use in contact with human cells, without any toxicity, irritation, undue allergic response and the like, and proportioned at a reasonable advantage/risk ratio.

Several examples of the invention will now be given by way of illustration and without in any way being limiting in nature.

Example:
Measurement of the Propigmenting Activity of the Combination of a Prostaglandin Agonist, and in Particular PGF2α, and of Two MC1R Receptor Agonists:

In mice, melanocytes are not present in the epidermis of the areas covered with hair and are mainly present in the hair follicles. The tail skin of SKH2 mice is pigmented, which is of particular interest for evaluating the effect of topical agents on skin pigmentation. The pigmentation modifications induced by these topical compounds can be quantified by various means, for instance the clinical score of the pigmentation and the measurement of the tail color using a colorimeter.

The evaluation of the propigmenting activity of 0.01% travoprost alone or in combination with MC1R receptor agonists: compound A at 7% or compound B at 8%, is carried out by topical application on the tail of SKH2 mice for 57 days. The treatment is carried out 5 days per week for 57 days. 20 µl of the test product diluted in the carrier 145 are applied to the tail. In the case of the combinations, 20 µl of the MC1R agonist solution are applied after the treatment with 20 µl of the 0.01% travoprost solution.

Figure 2:
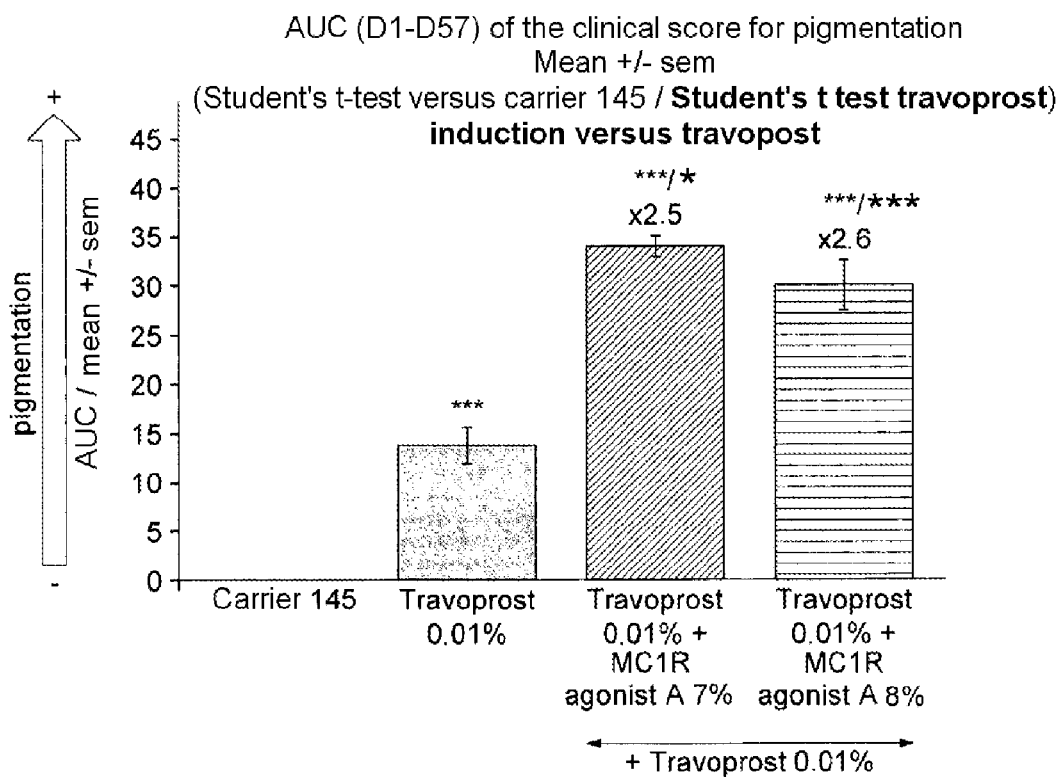

The clinical score of the animals is recorded once a week before irradiation; the pigmentation is evaluated by virtue of a score on a scale of 0 to 4. The scores are divided up as follows:
  0: natural pigmentation
  1: slight pigmentation
  2: moderate pigmentation
  3: marked pigmentation
  4: strong pigmentation The results of the evaluation of the pigmentation and of the statistical analysis are represented in FIGS. 1 and 2:
  Clinical Score for Pigmentation
  The following calculations are performed:
    Mean±sem of the clinical scores per week per treatment group (see FIG. 1).
    Areas under the curve (AUCs) of the clinical scores per animal from D1 to D57 (see FIG. 2).
    AUC increase index for each combination versus the travoprost group (see FIG. 2).

The AUC is obtained by calculating the sum of the areas of the rectangles between the first and the last day of the study. The various treatment groups are compared to the carrier group and to the 0.01% travoprost group with respect to this parameter by means of the Student's t test.

The results presented in figures 1 and 2 show that travoprost alone at 0.01% moderately increases the natural pigmentation of the tail skin as early as day 36 of the study, compared with the group treated with the carrier. The combination of 0.01% travoprost with the MC1R agonist A at 7% or the MC1R agonist B at 8% significantly increases the natural pigmentation of the skin compared with the group treated with the carrier and with the group treated with 0.01% travoprost alone. This synergistic effect is marked with two MC1R agonists.

Figure 3:
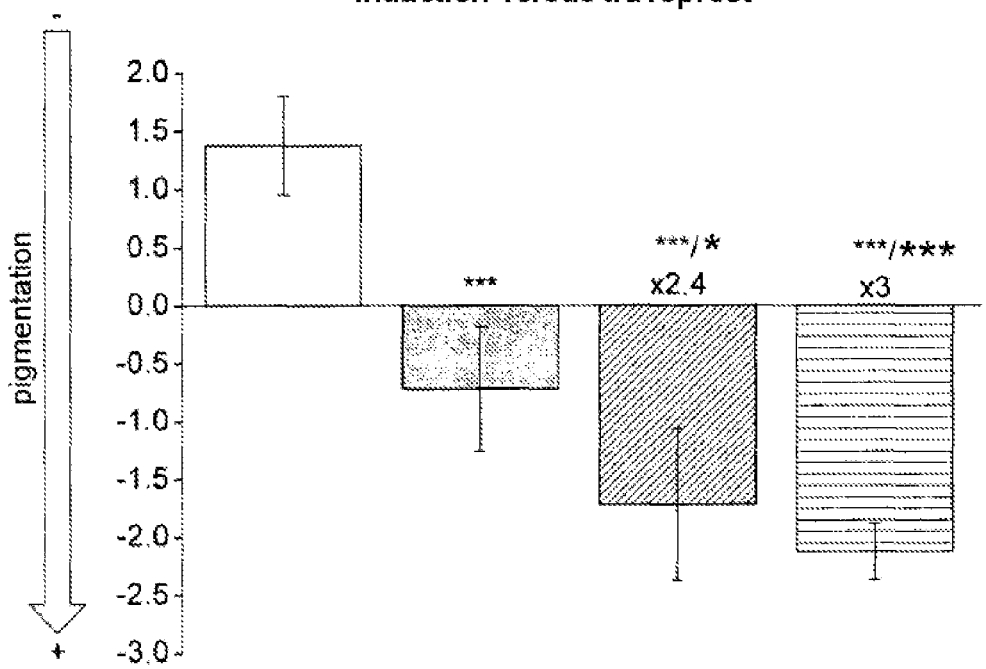

The Luminance Measurement Results are Presented in FIG. 3:

The following calculations are performed:
  Mean difference±sem in luminance (delta L*) between the beginning and the end of the study.
  Delta L increase index for each combination versus the travoprost group.

The results presented in FIG. 3 on the difference in luminance of the skin between the beginning and the end of the study confirm the results of the clinical scores for pigmentation and show a synergistic propigmenting effect of the combination of 0.01% travoprost with the MC1R agonists A and B.

The invention claimed is:

1. A combination product comprising at least one prostaglandin receptor agonist and at least one MC1R receptor agonist, as a medicament for use simultaneously, separately or spread out over time for the treatment of dermatological conditions linked to hypopigmentation,
   wherein the prostaglandin receptor agonist is present at a concentration of between approximately 0.001% and 1% by weight, relative to the total weight of a composition comprising the prostaglandin receptor agonist, and the MC1R receptor agonist is present at a concentration of between approximately 0.001% and 10% by weight, relative to the total weight of a composition comprising the MC1R receptor agonist.

2. The product as claimed in claim 1, wherein the dermatological conditions are selected from the group consisting of vitiligo, albinism, hypomelanosis, depigmentations caused by physical or chemical agents, post-inflammatory hypopigmentations, Sutton's phenomenon and other hypopigmentary lesions.

3. The product as claimed in claim 2, wherein the dermatological condition is vitiligo.

4. The product as claimed in claim 1, wherein the prostaglandin receptor agonist and the MC1R receptor agonist are present in the same composition.

5. The product as claimed in claim 1, wherein the prostaglandin receptor agonist and the MC1R receptor agonist are present separately from one another in distinct compositions.

6. The product as claimed in claim 5, wherein the composition comprising the prostaglandin receptor agonist is administered first, and the composition comprising the MC1R receptor agonist is administered second.

7. The product as claimed in claim 1, wherein the at least one prostaglandin receptor agonist is at a concentration of between approximately 0.004% and 0.04%, relative to the total weight of the composition comprising the prostaglandin receptor agonist, and the at least one MC1R receptor agonist is at a concentration of between approximately 5% and 10% by weight, relative to the total weight of the composition comprising the MC1R receptor agonist.

8. The product as claimed in claim 4, wherein the composition(s) is (are) administered topically.

9. The product as claimed in claim 8, wherein the composition(s) is (are) in the form of salves, creams, milks, ointments, powders, impregnated pads, syndets, solutions, gels, sprays, foams, suspensions, sticks, shampoos, washing bases or else suspensions of microspheres, nanospheres or lipid or polymeric vesicles, or polymeric or gelled patches for controlled release.

10. The product as claimed in claim 1, wherein the prostaglandin receptor agonist is a PGE or PGF agonist.

11. The product as claimed in claim 10, wherein the prostaglandin receptor agonist is a PGF2α agonist.

12. The product as claimed in claim 11, wherein the prostaglandin receptor agonist is selected from the group consisting of latanoprost, bimatoprost, travoprost, fluprostenol and unoprostone.

13. The product as claimed in claim 1, wherein the MC1R receptor agonist is selected from the group consisting of α, β or γ melanocyte-stimulating hormones (MSH), adrenocorticotropic hormone (ACTH) 1-39, β-lipotropin, β-endorphin and compounds of general formula (I) or (II) below:

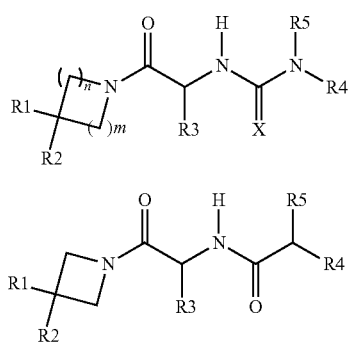

in which, for general formula (I):
R1 represents a hydrogen atom, an aryl, a substituted aryl, an alkyl, a cycloalkyl, a cycloalkylalkyl, or a cycloalkylalkylalkyl;
R2 represents a hydrogen atom, a hydroxyl, a lower alkyl, a substituted lower alkyl, a higher alkyl, a substituted higher alkyl, a cycloalkyl, a cycloalkylalkyl, a lower alkoxy, a substituted lower alkoxy, a higher alkoxy, a substituted higher alkoxy, a cycloalkylalkoxy, an acyloxy, an acyl, an alkoxycarbonyl, a carboxamide, a carboxylic acid, a cyano, or an amino disubstituted with an acyl and an aryl or alkyl;
R3 represents an aralkyl or a substituted aralkyl;
R4 represents a heteroaralkyl or a substituted heteroaralkyl;
R5 represents a hydrogen atom or an alkyl;
X represents an oxygen atom or a sulfur atom;
n and m may be equal to 1 or 2;
and also the corresponding salts and enantiomers;
or in which, for general formula (II):
R1 represents an aryl, a substituted aryl or a cycloalkyl;
R2 represents a hydrogen atom, a hydroxyl, a lower alkyl, a substituted lower alkyl, a higher alkyl, a substituted higher alkyl, a cycloalkyl, a cycloalkylalkyl which may be substituted, a lower alkoxy, a substituted lower alkoxy, a higher alkoxy, a substituted higher alkoxy, a cycloalkylalkoxy, or an acyloxy;
R3 represents an aralkyl or a substituted aralkyl;
R4 represents a heteroaralkyl, a substituted heteroaralkyl, a heteroalkyl or a substituted heteroalkyl;
R5 represents a hydrogen atom, a hydroxyl, an amino, an acylamino or a sulfonamide;
and also the corresponding salts and enantiomers.

14. The product as claimed in claim 13, wherein the MC1R receptor agonist is chosen from the compounds of general formula (II) in which:
R1 represents a cyclopropylm ethyl or a 4-hydroxybutyl group; and
R2 represents a hydrogen atom or a methyl group.

15. The product as claimed in claim 13, wherein the MC1R receptor agonist is selected from the group consisting of:

1-[(S)-2-(4-Butyryl-4-phenylpiperidin-1-yl)-1-(4-methoxybenzyl)-2-oxoethyl]-3[2-(1H-imidazol-4-yl)ethyl]urea;
1-[2-(1H-Imidazol-4-yl)ethyl]-3-[1-(4-methoxybenzyl)-2-oxo-2-(4-oxo-1 -phenyl-1,3,8-triazaspiro[4.5]dec-8-yl)ethyl]urea;
1-[2-(4-Cyano-4-phenylpiperidin-1-yl)-1-(4-methoxybenzyl)-2-oxoethyl]-3-[2-(1H-imidazol-4-yl)ethyl]urea;
1-[2-(1H-Imidazol-4-yl) ethyl]-3-[1-(4-methoxybenzyl)-2-oxo-2-(4-phenylpiperidin-1-yl)ethyl]urea;
1-[2-(1H-Imidazol-4-yl)ethyl]-3[1-(4-methoxybenzyl)-2-oxo-2-piperidin-1-ylethyl]urea;
Ethyl 4-cyclohexyl-1-[2-{3[2-(1H-imidazol-4-yl)ethyl]ureido}-3-(4-methoxyphenyl)propionyl]piperidin-4-carboxylate;
N-{1-[2-{3-[2-(1H-Imidazol-4-yl)ethyl]ureido}-3-(4-methoxyphenyl)propionyl]piperidin-4-yl}-N-phenyl-propionamide;
1[2-{3[2-(1H-Imidazol-4-yl)ethyl]ureido}-3-(4-methoxyphenyl)propionyl]-3-phenylazetidin-3-yl butyrate;
Ethyl 1-[2-{3-[2-(1H-imidazol-4-yl)ethyl]ureido}-3-(4-methoxyphenyl)propionyl]piperidine-4-carboxylate;
1-[2-(1H-Imidazol-4-yl)-ethyl]-3-{1-(4-methoxybenzyl)-2-[4-(2-methoxyphenyl)piperidin-1-yl]-2-oxoethyl}urea;
1-[2-(3-Butoxy-3-phenylazetidin-1-yl)-1-(4-methoxybenzyl)-2-oxoethyl]-3-[2-(1H-imidazol-4-yl)ethyl]urea;
Methyl 4-cyclohexyl-1-[2-{3-[2-(1H-imidazol-4-yl)ethyl]ureido}-3-(4-methoxyphenyl)propionyl]piperidine-4-carboxylamide;
1-[2-(3-Cyclohexanecarbonylazetidin-1-yl)-1-(4-methoxybenzyl)-2-oxoethyl]-3-[2-(1H-imidazol-4-yl)ethyl]urea;
Ethyl 4-cyclohexyl-1-[2-{3-ethyl-3-[2-(1H-imidazol-4-yl)ethyl]ureido}-3-(4-methoxyphenyl)propionyl]piperidine-4-carboxylate;
N-Cyclopropyl-N-{1-[2-{3-[2-(1H-imidazol-4-yl)ethyl]ureido}-3-(4-methoxyphenyl)propionyl]piperidin-4-yl}propionamide;
Ethyl 4-cyclohexyl-1-(2-{3-[2-(1H-imidazol-4-yl)ethyl]ureido}-3-phenylpropionyl)piperidine-4-carboxylate;
1-[2-(4-Butyryl-4-cyclohexylpiperidin-1-yl)-1-(4-methoxybenzyl)-2-oxoethyl]-3-[2-(3H-imidazol-4-yl)ethyl]urea;
1-[2-(4-Butoxy-4-cyclohexylpiperidin-1-yl)-1-(4-methoxybenzyl)-2-oxoethyl]-3-[2-(1H-imidazol-4-yl)ethyl]urea;
Ethyl 4-cyclohexyl-1-(2-{3-[2-(1H-imidazol-4-yl)ethyl]ureido}-2-phenylacetyl)piperidine-4-carboxylate;
Methyl 4-cyclohexyl-1-[2-{3-[2-(1H-imidazol-4-yl)ethyl]ureido}-3-(4-methoxyphenyl)propionyl]piperidine-4-carboxylate;
1-[2-(4-Cyclohexyl-4-ethoxypiperidin-1-yl)-1-(4-methoxybenzyl)-2-oxoethyl]-3-[2-(1H-imidazol-4-yl)ethyl]urea;
1-[2-(4-Acetyl-4-cyclohexylpiperidin-1-yl)-1-(4-methoxybenzyl)-2-oxoethyl]-3-[2-(1H-imidazol-4-yl)ethyl]urea;
Methyl 4-cyclohexyl-1-(2-{3-[2-(1H-imidazol-4-yl)ethyl]ureido}-2-phenylacetyl)piperidine-4-carboxylate;
Ethyl 4-ethyl-1-[2-{3-[2-(1H-imidazol-4-yl)ethyl]ureido}-3-(4-methoxyphenyl)propionyl]piperidine-4-carboxylate;

1-[2-(4-Cyclohexyl-4-propoxypiperidin-1-yl)-1-(4-methoxybenzyl)-2-oxoethyl]-3-[2-(1H-imidazol-4-yl)ethyl]urea;

4-Cyclohexyl-1-[2-{3-[2-(1H-imidazol-4-yl)ethyl]ureido}-3-(4-methoxyphenyl)propionyl]piperidine-4-carboxylic acid;

1-[2-(1H-Imidazol-4-yl)ethyl]-3-{1-(4-methoxybenzyl)-2-[3-(2-methylcyclohexyl)-3-propoxyazetidin-1-yl]-2-oxoethyl}urea;

Propyl 4-cyclohexyl-1-[2-{3-[2-(1H-imidazol-4-yl)ethyl]ureido}-3-(4-methoxyphenyl)propionyl]piperidine-4-carboxylate;

1-[2-(1H-Imidazol-4-yl)ethyl]-3-[1-(4-methoxybenzyl)-2-oxo-2-(3-pentyl-3-phenylazetidin-1-yl)ethyl]urea;

Ethyl 1-((R)-3-(4-chlorophenyl)-2-{3-[2-(1H-imidazol-4-yl)ethyl]ureido}propionyl)-4-cyclohexylpiperidine-4-carboxylate;

Ethyl 1-((S)-3-(4-chlorophenyl)-2-{3-[2-(1H-imidazol-4-yl)ethyl]ureido}propionyl)-4-cyclohexylpiperidine-4-carboxylate;

1-[2-(4-cyclohexyl-4-propionylpiperidin-1-yl)-1-(4-methoxybenzyl)-2-oxoethyl]-3-[2-(1H-imidazol-4-yl)ethyl]urea;

1-[2-(4-Cyclohexyl-4-propionylpiperidin-1-yl)-1-(4-methoxybenzyl)-2-oxoethyl]-3-(1H-imidazol-4-ylmethyl)urea;

Ethyl 4-cyclohexyl-1-[(R)-2-{3-[2-(1H-imidazol-4-yl)ethyl]ureido}-3-(4-methoxyphenyl)propionyl]piperidine-4-carboxylate;

Ethyl 4-cyclopropylmethyl-1-[2-{3-[2-(1H-imidazol-4-yl)ethyl]ureido}-3-(4-methoxyphenyl)propionyl]piperidine-4-carboxylate;

Propyl 4-cyclohexyl-1-(2-{3-[2-(1H-imidazol-4-yl)ethyl]ureido}-3-phenylpropionyl)piperidine-4-carboxylate;

Ethyl 4-cyclopentyl-1-(2-{3-[2-(1H-imidazol-4-yl)ethyl]ureido}-3-phenylpropionyl)piperidine-4-carboxylate;

Ethyl 4-cyclopentyl-1-[2-{3-[2-(1H-imidazol-4-yl)ethyl]ureido}-3-(4-methoxyphenyl)propionyl]piperidine-4-carboxylate;

Ethyl 4-cyclohexyl-1-[(S)-2-{3-[2-(1H-imidazol-4-yl)ethyl]ureido}-3-(4-methoxyphenyl)propionyl]piperidine-4-carboxylate;

1-[(R)-2-(4-Butyryl-4-cyclohexylpiperidin-1-yl)-1-(4-methoxybenzyl)-2-oxoethyl]-3-[2-(1H-imidazol-4-yl)ethyl]urea;

1-[(R)-2(4-Butyryl-4-cyclohexylpiperidin-1-yl)-1-(4-fluorobenzyl)-2-oxoethyl]-3-[2-(1H-imidazol-4-yl)ethyl]urea;

1-[(R)-1-Benzyl-2-(4-butyryl-4-cyclohexylpiperidin-1-yl)-2-oxoethyl]-3-[2-(1H-imidazol-4-yl)ethyl]urea;

1-[(R)-2-(4-Butyryl-4-cyclohexylpiperidin-1-yl)-1-(4-methoxybenzyl)-2-oxoethyl]-3-[2-(3-methyl-3H-imidazol-4-yl)ethyl]urea;

1-[(R)-2-(4-Butyryl-4-cyclohexylpiperidin-1-yl)-1-(4-chlorobenzyl)-2-oxoethyl]-3-[2-(1H-imidazol-4-yl)ethyl]urea;

Ethyl 4-cyclohexyl-1-((R)-3-(3,4-dichlorophenyl)-2-{3-[3-(1H-imidazol-4-yl)propyl]ureido}propionyl)piperidine-4-carboxylate;

Ethyl 4-cyclohexyl-1-((R)-3-(4-methoxyphenyl)-2-{3-[2-(3-methyl-3H-imidazol-4-yl)ethyl]ureido}propionyl)piperidine-4-carboxylate;

Ethyl 4-cyclohexyl-1-[(R)-2-{3-[2-(1H-imidazol-4-yl)ethyl]thioureido}-3-(4-methoxyphenyl)propionyl]piperidine-4-carboxylate;

1-[(R)-2-(4-Butyryl-4-cyclohexylpiperidin-1-yl)-1-(4-methoxybenzyl)-2-oxoethyl]-3-[2-(1H-imidazol-4-yl)ethyl]thiourea;

1-[(R)-2-(4-Cyclohexyl-4-propoxypiperidin-1-yl)-1-(4-methoxybenzyl)-2-oxoethyl]-3-[2-(1H-imidazol-4-yl)ethyl]thiourea;

1-[(R)-1-Benzyl-2-(4-cyclohexyl-4-propoxypiperidin-1-yl)-2-oxoethyl]-3-[2-(1H-imidazol-4-yl)ethyl]thiourea;

1-[(R)-1-Benzyl-2-(4-cyclohexyl-4-propoxypiperidin-1-yl)-2-oxoethyl]-3-[2-(1H-imidazol-4-yl)ethyl]urea;

Ethyl 4-cyclohexyl-1-((R)-3-(4-methoxyphenyl)-2-{3-[2-(3-methyl-3H-imidazol-4-yl)ethyl]thioureido}propionyl)piperidine-4-carboxylate;

Ethyl 4-cyclohexyl-1-((R)-2-{3-[2-(3-methyl-3H-imidazol-4-yl)ethyl]ureido}-3-phenylpropionyl)piperidine-4-carboxylate;

1-[(R)-2-(4-Cyclohexyl-4-propoxypiperidin-1-yl)-1-(4-methoxybenzyl)-2-oxoethy]-3-[2-(3-methyl-3H-imidazol-4-yl)ethyl]urea;

Ethyl 1-((R)-3-(4-chlorophenyl)-2-{3-[2-(3-methyl-3H-imidazol-4-yl)ethyl]ureido}propionyl)-4-cyclohexylpiperidine-4-carboxylate;

Ethyl 4-cyclohexyl-1-((R)-3-(4-fluorophenyl)-2-{3-[2-(3-methyl-3H-imidazol-4-yl)ethyl]ureido}propionyl)piperidine-4-carboxylate;

Ethyl 4-cyclohexyl-1-((R)-3-(4-fluorophenyl)-2-{3-[2-(1H-imidazol-4-yl)ethyl]ureido}propionyl)piperidine-4-carboxylate;

Ethyl 4-cyclohexyl-1-((R)-3-(4-fluorophenyl)-2-{3-[2-(1H-imidazol-4-yl)ethyl]thioureido}propionyl)piperidine-4-carboxylate;

Ethyl 1-((R)-3-(4-chlorophenyl)-2-{3-[2-(H-imidazol-4-yl)ethyl]thioureido}propionyl)-4-cyclohexylpiperidine-4-carboxylate;

Ethyl 1-((R)-3-(4-chlorophenyl)-2-{3-[2-(3-methyl-3H-imidazol-4-yl)ethyl]thioureido}propionyl)-4-cyclohexyipiperidine-4-carboxylate;

1-[(R)-2-(4-Cyclohexyl-4-propoxypiperidin-1-yl)-1-(4-fluorobenzyl)-2-oxoethyl]-3-[2-(1H-imidazol-4-yl)ethyl]urea;

1-[(R)-1-(4-Chlorobenzyl)-2-(4-cyclohexyl-4-propoxypiperidin-1-yl)-2-oxoethyl]-3-[2-(1H-imidazol-4-yl)ethyl]urea;

N-[(R)-2-[3-(4-Hydroxybutoxy)-3-o-tolylazetidin-1-yl]-1-(4-methoxybenzyl)-2-oxoethyl]-3-(-1H-imidazol-4-yl)propionamide;

N-[(R)-2-(3-Cyclopropylmethoxy-3-o-tolylazetidin-1-yl)-1-(4-methoxybenzyl)-2-oxoethyl]-3-(5-methyl-1H-imidazol-4-yl)propionamide;

and also the respective salts and enantiomers thereof.

16. The product as claimed in claim 14, wherein the MC1R receptor agonists are selected from the group consisting of:

Ethyl 4-cyclohexyl-1-[(R)-2-{3-[2-(1H-imidazol-4-yl)ethyl]ureido}-3-(4-methoxyphenyl)propionyl]piperidine-4-carboxylate;

N-[(R)-2-[3-(4-Hydroxybutoxy)-3-o-tolylazetidin-1-yl]-1-(4-methoxybenzyl)-2-oxoethyl]-3-(-1H-imidazol-4-yl)propionamide;

N-[(R)-2-(3-Cyclopropylmethoxy-3-o-tolylazetidin-1-yl)-1-(4-methoxybenzyl)-2-oxoethyl]-3-(5-methyl-1H-imidazol-4-yl)propionamide, and also the corresponding salts and enantiomers.

17. A composition comprising at least one MC1R receptor agonist and at least one prostaglandin receptor agonist, in a physiologically acceptable carrier, wherein the prostaglandin receptor agonist is present at a concentration of between approximately 0.001% and 1% by weight, relative to the total weight of the composition comprising the prostaglandin receptor agonist, and the MC1R receptor agonist is present at a concentration of between approximately 0.001% and 10% by weight, relative to the total weight of the composition comprising the MC1R receptor agonist.

18. The product as claimed in claim 12, wherein the prostaglandin receptor agonist is travoprost.

* * * * *